United States Patent [19]

Gorski et al.

[11] Patent Number: 4,580,682

[45] Date of Patent: Apr. 8, 1986

[54] SELF-CONTAINED INDICATOR DEVICE

[75] Inventors: Theodore W. Gorski; Richard F. Wallin, both of Perrysburg, Ohio

[73] Assignee: North American Science Associates, Inc., Norwalk, Ohio

[21] Appl. No.: 462,516

[22] Filed: Jan. 31, 1983

[51] Int. Cl.⁴ .................... B65D 25/08; B65D 81/32
[52] U.S. Cl. .................................. 206/569; 206/216; 206/219; 206/222; 220/258; 435/31; 436/1
[58] Field of Search ............... 206/219, 222, 569, 216, 206/221; 220/258; 435/31; 422/58; 436/1

[56] References Cited

U.S. PATENT DOCUMENTS

| | | | |
|---|---|---|---|
| 3,134,725 | 5/1964 | Brook et al. | 435/31 |
| 3,255,926 | 6/1966 | Modderno . | |
| 3,378,168 | 4/1968 | Hildebrandt | 206/222 |
| 3,402,855 | 9/1968 | Schroeder et al. . | |
| 3,440,144 | 4/1969 | Anderson | 435/31 |
| 3,613,955 | 10/1971 | Wetherell, Jr. | 206/222 |
| 3,661,717 | 5/1972 | Nelson | 435/31 |
| 3,762,540 | 10/1973 | Bauman et al. | 206/219 |
| 3,968,872 | 7/1976 | Cavazza | 206/222 |
| 4,136,775 | 1/1979 | Zaltzman | 206/219 |
| 4,304,869 | 12/1981 | Dyke | 206/219 |
| 4,311,793 | 1/1982 | Halleck . | |
| 4,314,030 | 2/1982 | Habich . | |
| 4,348,209 | 9/1982 | Murtaugh et al. . | |
| 4,355,113 | 10/1982 | Mennen . | |

FOREIGN PATENT DOCUMENTS

078112A2  9/1981  European Pat. Off. .
 78112     5/1983  European Pat. Off. .............. 435/31

Primary Examiner—William Price
Assistant Examiner—Brenda J. Ehrhardt
Attorney, Agent, or Firm—Emch, Schaffer, Schaub & Porcello Co.

[57] ABSTRACT

The application discloses a test vial including a test article for immersion into a fluid medium, a sealed chamber which contains the fluid medium, and an open chamber which is external to the sealed chamber and which supports the test article. The sealed and open chambers define a barrier which isolates the fluid medium from the test article. The open chamber is covered by a closure. Retaining means are positioned on the open chamber and on the closure. The retaining means cooperatively support the closure in a first position and cooperatively receive the closure in a second position. The closure has a means for detaching the barrier from the open and sealed chambers and for injecting the test article in the fluid medium when the closure is moved from the first position to the second position.

4 Claims, 17 Drawing Figures

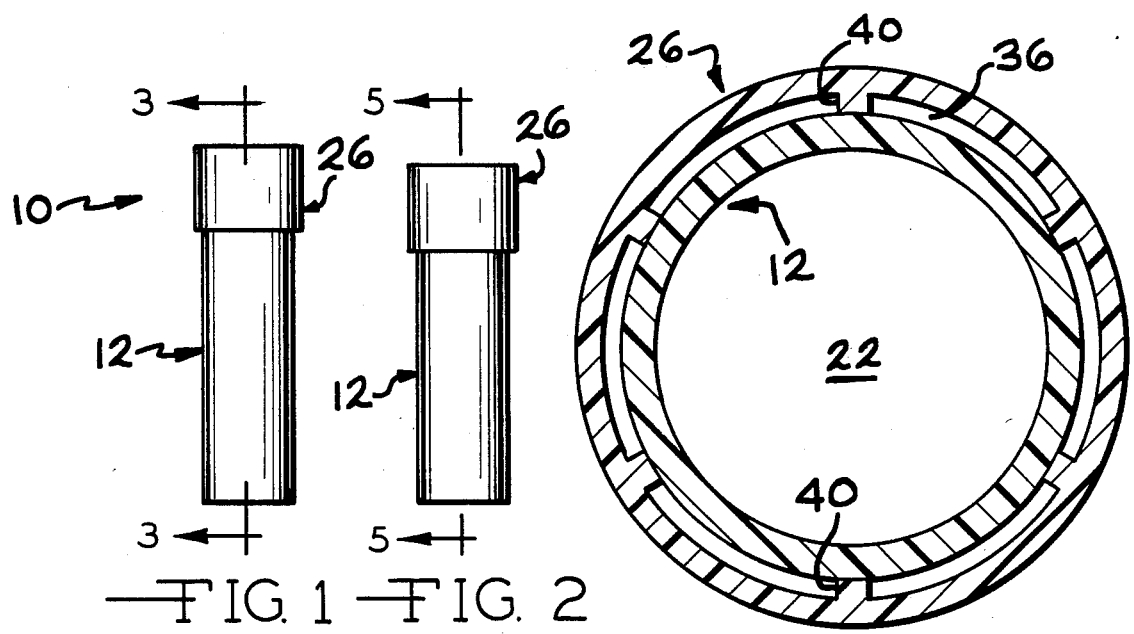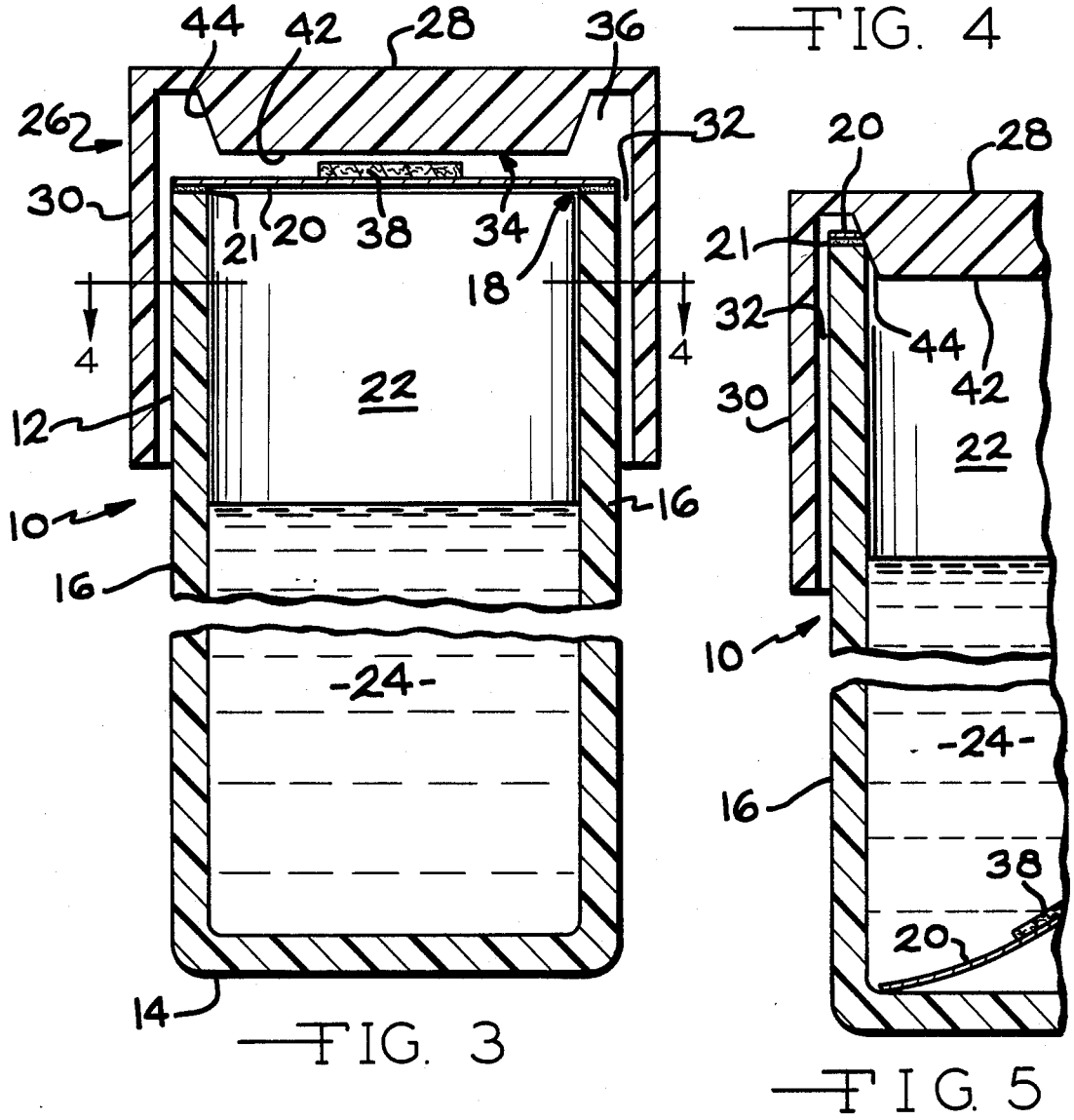

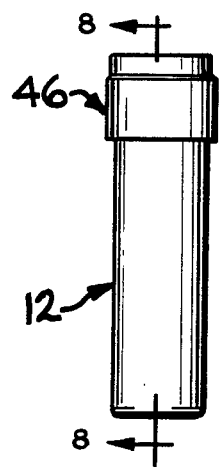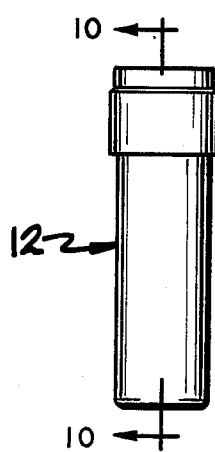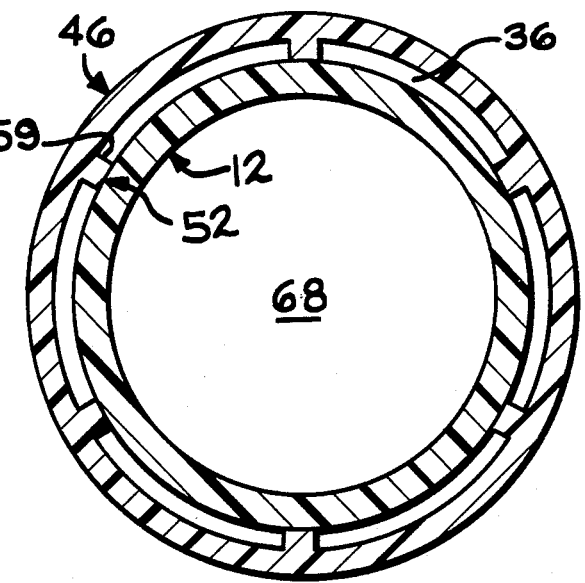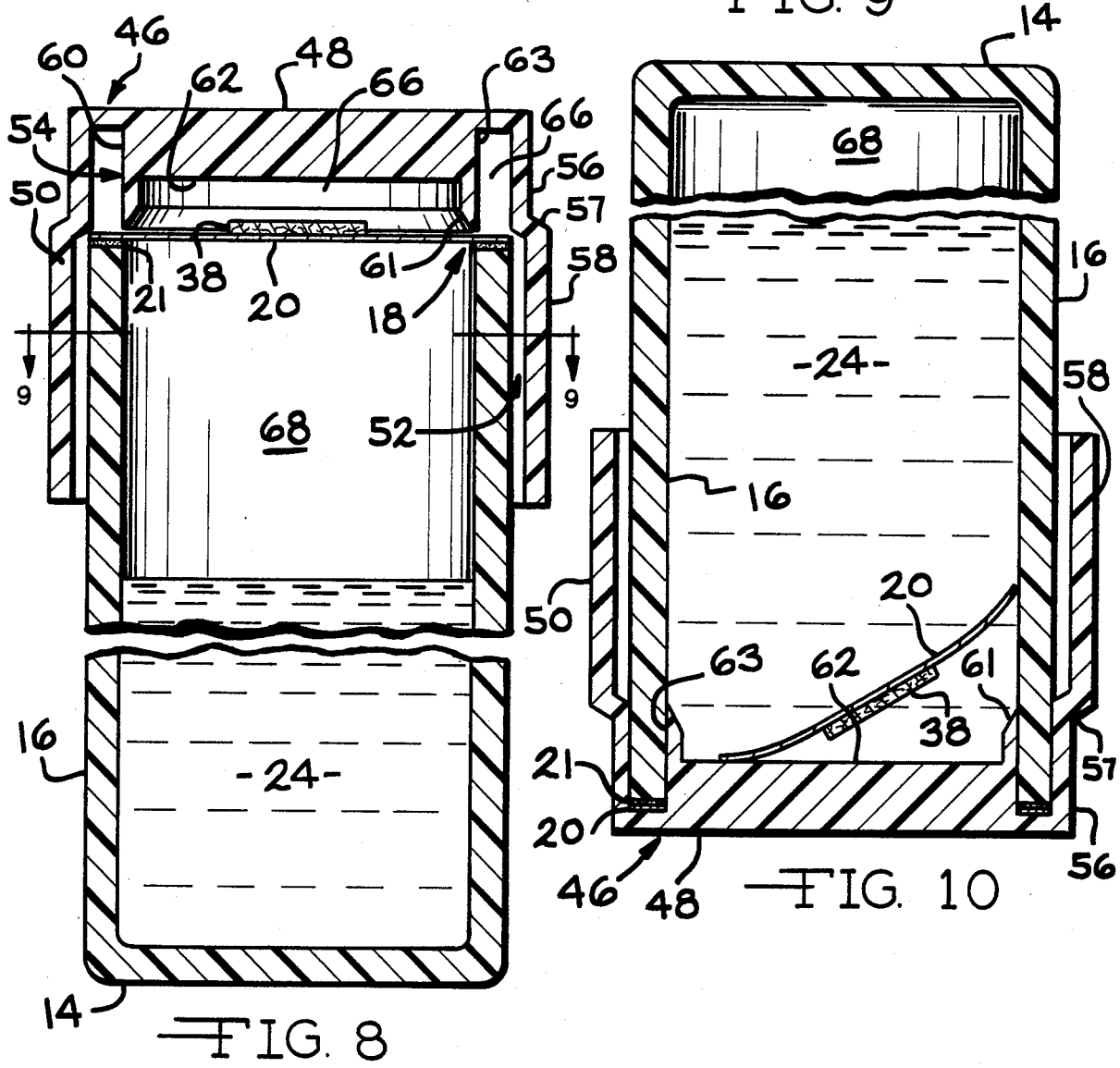

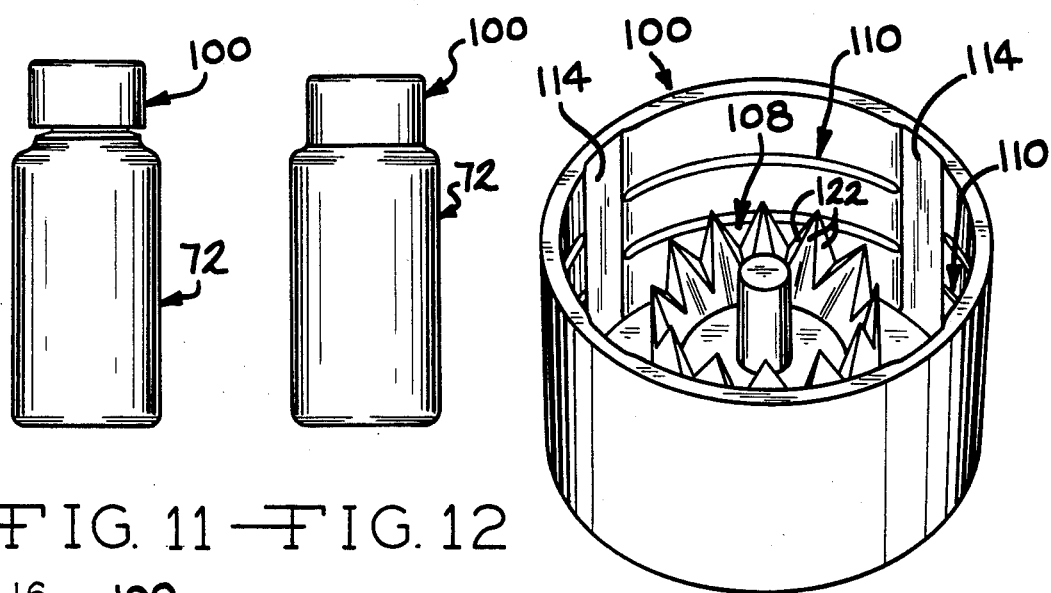
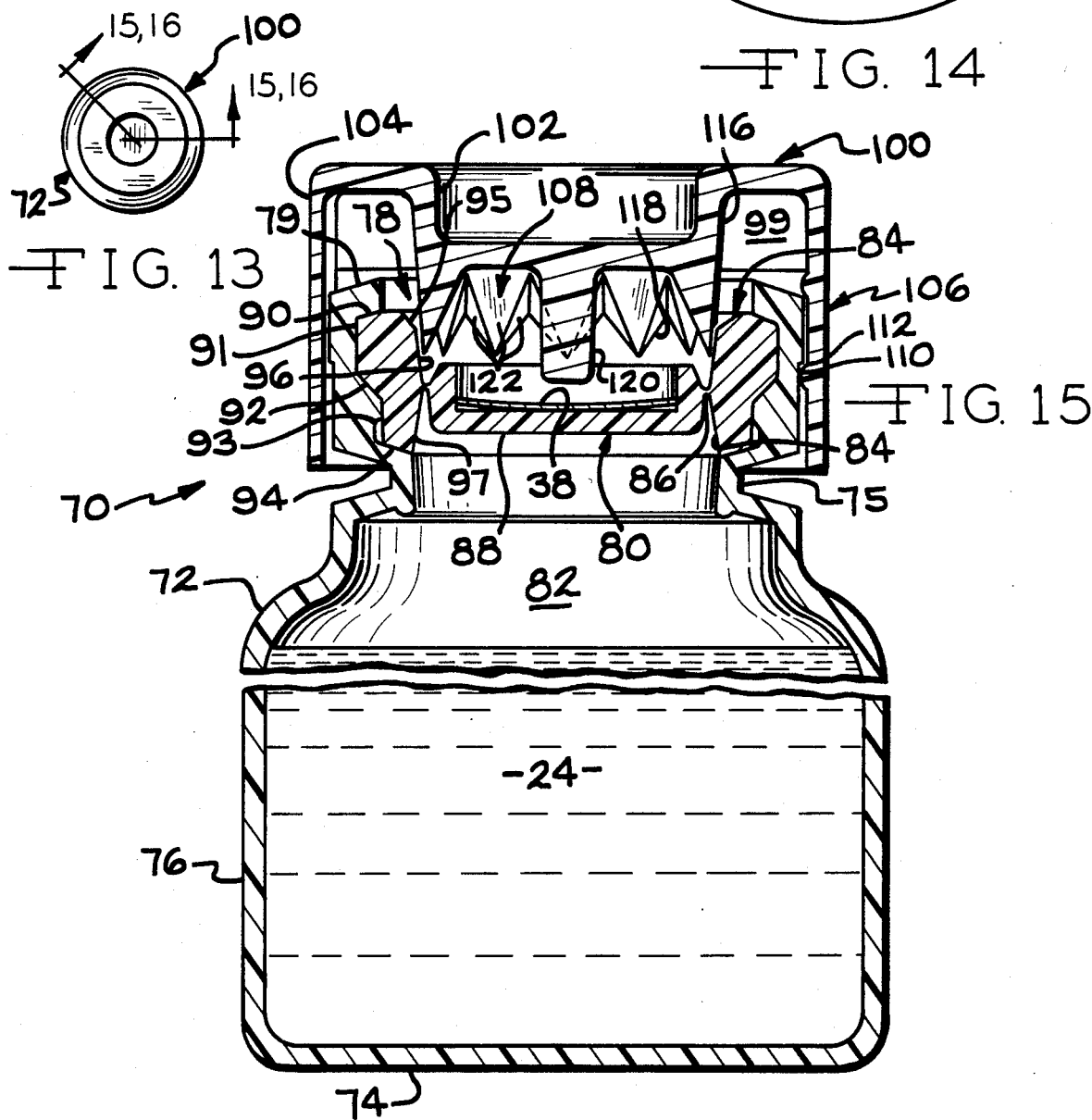

SELF-CONTAINED INDICATOR DEVICE

BACKGROUND OF THE INVENTION

The invention is a self-contained apparatus for use in determining the presence or absence of a biological or chemical substance within a test environment. Prior art tests for determining, for example, the presence of chemical substances or micro-organisms in water and air or the effectiveness of steam or gas sterilization equipment typically require rigid standardized procedures which can only be performed by highly qualified personnel.

A common test for sterilization effectiveness is performed by a technician who first places an absorbent paper test strip which is impregnated with a predetermined number and species of live micro-organisms in a sertilization chamber along with objects to be sterilized. The test strip and the objects are then subjected to a sterilization medium such as steam, gas or radiation. Once the sterilization cycle is completed, the technician removes the test strip from the sterilization chamber and places it in a sterile culture medium. The micro-organisms on the test strip are then incubated in the culture medium for a predetermined period of time. The technician then examines the medium to determine whether any micro-organisms on the test strip survived sterilization. Any observable change in color, appearance or turbidity etc., of the medium may indicate that sterilization was not successful.

This above-described sterility test can only be carried out by a skillful technician who is capable of avoiding contamination of the test strip during the various manipulative steps of the test. Similarly, other known tests for the presence or absence of a chemical or biological substances in a test medium requiring the manipulation of a test article require skill to avoid contamination of the test article during the test procedure.

The present invention is a self-contained test apparatus which eliminates potentials for contamination during the test procedure described above. The invention also presents solutions to shortcomings encountered by self contained test apparatus known to applicants:

U.S. Pat. No. 3,440,144, assigned to H. W. Anderson Products, Inc., relates to a package containing a spore strip, a frangible ampule containing a culture medium, a flexible sleeve, and a flexible semi-permeable bag. The frangible ampule has an open spout connected to the body of the ampule by a neck. Sterile culture medium is placed within the ampule through the opening in the spout. The spout is heat sealed, forming a closed ampule. The ampule is then sterilized and placed within the flexible sleeve along with the spore strip. The sleeve is then placed within the flexible bag and the ends of the bag are heat sealed. The bag is then placed in the sterilization chamber along with the objects to be sterilized. Once the sterilization cycle is completed the technician removes the bag from the chamber, grasps the sleeve containing the ampule and spore strip through the bag, and breaks the spout off at the neck of the ampule releasing the culture medium but avoiding tearing the sleeve and the bag with the shards of the ampule. The bag is placed in an incubator for a predetermined period of time. The technician then examines the medium to determine whether any microorganisms survived the sterilization cycle. The technician must use care throughout this test in order not to prematurely break the ampule or rupture the flexible, semi-permeable bag.

A further disadvantage, not dependent upon the skill of the technician, is apparent in using this sterility test. During the sterilization cycle, the sterilant permeates the bag and kills the microorganisms. However, not all the sterilant passes through the bag. The bag entraps and retains some of the sterilant. After the bag is removed from the sterilization chamber the sterilant continues to diffuse from the bag into the culture medium. The additional sterilant in the culture medium may inhibit and kill the growth of any micro-organisms that have survived the sterility test. Thus, there is a danger that the test apparatus will show a false sterility result.

The U.S. Pat. No. 3,440,144 also relates to a flexible permeable bag sealed at both ends. Culture medium is sealed in one end of the bag and a spore strip is sealed in the other end of the bag. The bag is placed in the sterilization chamber along with the objects to be sterilized. After the sterilization cycle is completed the technician removes the bag from the chamber and squeezes the end of the bag containing the culture medium. The culture medium is forced into the end of the bag containing the spore strip. The bag is then placed in the incubator for a predetermined time, and observed for signs of micro-organism growth. A disadvantage to this test is that the bag does not provide for the direct exposure of the spore strip to the sterilant when the bag is in the sterilization chamber. The bag acts as a shelter for the micro-organisms and may allow some of the micro-organisms to survive the sterility test.

The U.S. Pat. No. 3,661,717, assigned to the Minnesota Mining and Manufacturing Company, relates to a sterility indicator containing a spore strip, a frangible ampule containing a culture medium, a flexible tube, and a gas permeable cap. The spore strip and the ampule are placed in the tube. The ampule fits snugly within the tube such that very little of the volume of the tube is unoccupied. The gas permeable cap is placed over the open end of the tube. The tube is then placed within the sterilization chamber along with the objects to be sterilized. Once the sterilization cycle is completed the technician removes the tube from the sterilization chamber and pinches the tube between the thumb and forefinger crushing the ampule and releasing the culture medium onto the spore strip. The tube is then placed in an incubator for a predetermined time and observed for signs of micro-organism growth. A disadvantage to this prior art is that the cap does not provide for direct exposure of the spore strip to the sterilant when the tube is in the sterilization chamber. Some of the micro-organisms are sheltered and may survive the sterilization. The survival of micro-organisms after the sterilization cycle indicates that the other objects in the chamber were not completely sterilized. When the sterilant does not penetrate through the cap sufficiently to kill the micro-organisms and micro-organisms survive, a false indication of non-sterility results.

The 3M Company markets a prior art product called "Attest" which includes a spore strip, a frangible ampule containing a culture medium, a flexible tube, and a gas permeable cap. The spore strip is placed in the tube. The ampule is placed within the tube and rests on the spore strip. The gas permeable cap is placed over the tube. The tube is then placed within the sterilization chamber along with the objects to be sterilized. Once the sterilization cycle is completed the technician removes the tube from the sterilization chamber and pinches the tube crushing the ampule and releasing the culture medium onto the spore strip. The tube is then placed in an incubator for a predetermined time and observed for signs of micro-organism growth. A disadvantage to this prior art is that the spore strip is located in the bottom of the tube and a sufficient amount of sterilant may not penetrate down into the bottom of the tube. Thus, some micro-organisms may not be killed, and a false indication of non-sterility results. Another disadvantage to this prior art product is that the lack of a real seal causes the medium to leak through the gas permeable cap after the ampule has been crushed.

Another prior art product, marketed as "PROOF" by American Sterilizer Company, Inc., includes a spore disc, a glass ampule containing a culture medium, a tube having one open end, and a cap containing downwardly extending legs. The spore disc and the ampule are placed within the tube. The ampule fits snugly within the tube. The cap rests on the open end of the tube. The legs on the cap extend into the tube and abut the top of the ampule. The tube is then placed within the sterilization chamber along with the objects to be sterilized. Once the sterilization cycle is completed the technician removes the tube from the sterilization chamber and pushes the cap down on the tube. The legs on the cap exert a force and crush the ampule releasing the culture medium onto the spore disc. The product is then placed in an incubator for a predetermined time and observed for signs of micro-organism growth. However, since the legs on the cap must be long and thick enough to have sufficient force to crush the ampule, the tube must be long in comparison to the length of the legs. Other disadvantages of the prior art known to applicants are that the imperfectly sealed containers permit spillage of the culture medium. The spillage may result in the spreading of the contaminated culture medium. Also, the ampules of the prior art products contain a small volume of culture medium such that, when the prior art product is placed in the incubator, the elevated temperatures of the incubator enhance evaporation of the culture medium. The volume of culture medium is so small that the culture medium evaporates before incubation is complete. Thus, the prior art product may be dried out unless it is placed in a humidified incubator. In addition, the spore carrier in the prior art products is positioned immediately adjacent the ampule in the tube. When the prior art product is placed in the sterilization chamber the ampule acts as a thermal insulator for the spore carrier. Some of the micro-organisms are protected from the sterilant and may survive sterilization.

SUMMARY OF THE INVENTION

The invention is directed to a test vial which consists of a container having substantially translucent walls and an initially open end, a rupturable member for closing the open end of the container and confining within the container a measured quantity of culture medium, and a closure for the container.

The closure and container have cooperating retaining means for holding the closure in place on the container in a first position with the closure telescoped over the end of the container. In this first position the closure and the container define an open chamber that is isolated from the culture medium by the rupturable member. In one embodiment of the invention, there is a measured number of selected viable bacterial spores on a filter paper carrier in the open chamber.

There are openings connecting the chamber to the atmosphere when the closure is in the first position on the container end. The retaining means may be overcome by moving the closure to a second position in which the closure is telescoped farther onto the end of the container.

The closure has an interior, axially extending portion which breaks the rupturable member thus placing the spores in the culture medium when the closure is moved axially to the second position. The closure also has an annular sealing element which closes the end of the container and isolates the culture medium and the spores from the atmosphere when the closure is moved to the second position.

The closure and container can have cooperating means for indicating when the closure is moved to second position and for retaining the closure in such second position.

BRIEF DESCRIPTION OF THE DRAWINGS

FIG. 1 is an elevation view of a first embodiment of the invention in a first position.

FIG. 2 is an elevation view of the embodiment shown in FIG. 1 in a second position.

FIG. 3 is a view taken along the line 3—3 in FIG. 1.

FIG. 4 is a view taken along the line 4—4 in FIG. 3.

FIG. 5 is a fragmentary view taken along the line 5—5 in FIG. 2.

FIG. 6 is an elevation view of a second embodiment of the invention in a first position.

FIG. 7 is an elevation view of the embodiment shown in FIG. 6 in a second position.

FIG. 8 is a view taken along the line 8—8 in FIG. 6.

FIG. 9 is a view taken along the line 9—9 in FIG. 8.

FIG. 10 is a view taken along the line 10—10 in FIG. 7 showing the invention in an inverted position.

FIG. 11 is an elevation view of a third embodiment of the invention in a first position.

FIG. 12 is an elevation view of the embodiment shown in FIG. 11 in a second position.

FIG. 13 is a plan view of the invention shown in FIGS. 11 and 12.

FIG. 14 is a perspective view of a closure of the embodiment shown in FIG. 11.

FIG. 15 is a view taken along the line 15—15 in FIG. 13.

DESCRIPTION OF THE PREFERRED EMBODIMENTS

Figure 16:
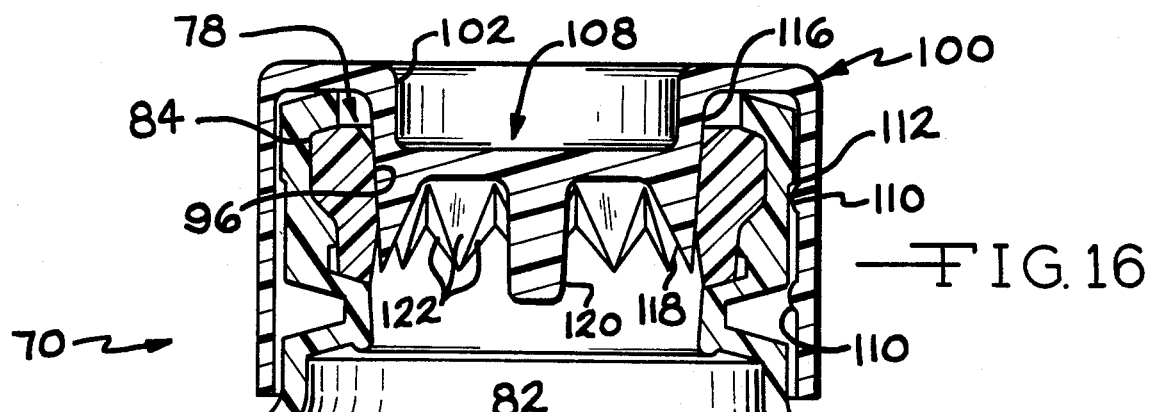
FIG. 16 is a view taken along the line 16—16 in FIG. 13 showing the embodiment in a second position.

The invention is directed to a test vial for use in detecting the presence or absence of a substance in an environment to be tested. Referring to FIGS. 1-5, the test vial 10 generally consists of an initially open container 12, a barrier means 20, and a cap or closure 26. The container 12 is shown as being substantially cylindrical in shape, but it should be understood that other shapes can be used without departing from the scope of the invention. The container 12 can be made from any generally translucent material, including glass or a plastic material such as a polypropylene material. The volume of the container 12 is defined by the capacity requirements of the test for which it is to be used, as will be explained below.

The container 12 generally has a closed end 14, side walls 16, and an open end 18. The open end 18 is closed by a barrier 20. The barrier 20 comprises an impermeable material, such as metal foil or a plastic material as, for example, polypropylene. The barrier 20 can be attached to the container 12 by sealing 21, including an adhesive material, or can be integrally molded to the side walls 16 as is disclosed as part of the embodiment of the invention depicted in FIGS. 12-17.

The barrier 20, the side walls 16 and the closed end 14 of the container 12 define a sealed chamber 22. The barrier 20 acts to confine within the sealed chamber 22 a measured quantity of a fluid medium 24. The fluid medium 24 can comprise any fluid material, including a liquid bacterial culture medium, such as a tryptic soy broth, or a gaseous chemical indicator. The fluid medium 24 is isolated from any external environment by the sealed chamber 22.

The closure or cap 26 is positioned adjacent the open end 18 and the barrier 20 of the container 12. The closure 26 is constructed to axially fit around the open end 18 of the container 12. The closure 26 can be made of any substantially hard material, including a hard plastic material such a polycarbonate or a hard elastomeric material such as a neoprene. The closure 26 includes a top portion 28, a side wall 30, a retaining portion 32, and a detaching element 34.

The closure 26 is positioned adjacent the open end 18 such that the side wall 30 extends from the top portion 28 in a direction towards the closed end 14 of the container 12. The top portion 28, the side wall 30 and the barrier 20 define an open chamber 36. The open chamber 36 is in communication with any outside environment.

A test article 38 is placed within the open chamber 36. The test article 38 can rest on the barrier 20. The test article 38 comprises any suitable material such as an absorbent paper such as filter paper which may be impregnated with spores or a chemical reactant, liquid or solid.

The closure 26 is held in a first position by the retaining means 32. As shown in FIGS. 1-5, the retaining means 32 consists of a plurality of longitudinally extending ribs 40 positioned on the interior side of the side wall 30. The ribs 40 frictionally engage the exterior of the side wall 16 of the container 12. A gas permeable tape (not shown) can be positioned around the closure 26 and the container 12 at the point where the side wall 30 of the closure 26 terminates. The gas permeable tape (not shown) provides a selective barrier against the environment to the open chamber 36 if the particular test so requires.

The detaching means 34 axially extends from the top portion 28 of the closure 26 in a direction towards the barrier 20. The detaching means 34 of the first embodiment of the invention, as shown in FIGS. 1-5, has a frustoconical shape and includes a base 42 and a sloped surface 44. The sloped surface 44 extends from the top portion 28 of the closure 26 at an acute angle such that the area of the base 42 is smaller than the area defined by the open end 18 of the container 12.

The operation of the test device of the invention is as follows: If for example, the test vial 10 is employed in the performance of sterility tests, the test article 38 comprises a strip of porous paper impregnated with spores or other micro-organisms. The medium 24 is a growth medium, such as tryptic soy broth, and may have a chemical indicator, such as phenol red. Referring to Fig. 3, the test vial 10 is in its first, ready position for use in a particular test such as a sterility test. The sterility test is conducted with the test vial 10 of the invention by placing the test vial 10 in a sterilization chamber along with articles to be sterilized. The test vial 10 and the objects are exposed to a sterilant such as steam, ethylene oxide or radiation. The sterilant enters the open chamber 36 and contacts the test article 38. The sterilant does not penetrate the barrier 20 or enter the sealed chamber 22. If sterilization is complete, the sterilant kills the organisms on the test article 38.

After the test vial 10 is removed from the tested sterilization chamber, manual pressure is applied to the top portion 28 of the closure 26. The closure 26 is axially moved in a direction towards the barrier 20. As the closure 26 telescopes on the container 12 the base 42 of the detaching means 34 comes into contact with the test article 38 and the barrier 20. As further pressure is applied the detaching means 34 acts to break the barrier 20. The barrier 20 and test article 38 are driven into the sealed chamber 22 and fall into the medium 24. As the closure 26 is further telescoped on the container 12 the sloped surface 44 of the detaching means 34 comes into contact with the open end 18 of the container 12 forming a seal.

The test vial 10 is incubated at optimal temperatures and the medium 24 is observed to find signs of bacterial growth. The signs of bacterial growth would be evidenced by turbidity of the medium 24 or color changes in the chemical indicator. The translucence of the container 12 aids in determining the end points of the test.

Another use of the test vial 10 includes the sampling of a water environment for the presence of a particular chemical or organism. The test vial 10 is submerged in the water environment. The water enters the open chamber 36 and contacts the test article 38. When employed as a water test device the test article 38 is a substantially sterile strip of filter paper. After the test article 38 is saturated with the water and whatever chemicals or organisms are present in the water, the test vial 10 is removed from the water environment. The closure 26 is moved to the second position injecting the test article 38 into the sealed chamber 22. The sealed chamber 22 contains a medium 24 which indicates the presence of a specific chemical or organism.

In FIGS. 6-10 a second embodiment of the invention is shown. The closure 46 includes a top portion 48, a wall 50, retaining means 52 and detaching means 54. The wall 50 has a first section 56, as shown in FIGS. 8 and 10, which extends perpendicularly from the top portion 48. A second section 57 of the wall 50 extends from the first section 56 at an acute angle away from the container 12. A third section 58 extends from the second section 57 in a plane parallel to the first section 56. The retaining means 52 includes a plurality of longitudinally extending ribs 59 which are positioned on the interior surface of the third section 58 of the wall 50. The retaining means 52 acts to hold the closure 46 in a first position.

The detaching means 54 axially extends from the top portion 48 in a direction toward the barrier 20. The detaching means 54 includes a depending annular skirt 60, an edge 61, and a base 62. The depending annular skirt 60 extends perpendicularly from the top portion 48 and is parallel to the first section 56 of the wall 50. The annular skirt 60 extends beyond the base 62 of the detaching means 54. The leading edge 61 of the skirt 60 is wedge-shaped. When the closure 46 is in the first position, an open chamber 66 is formed by the base 62, the barrier 20 and the sections 46, 57, 58 of the wall 50.

In operation, manual pressure is applied to the top portion 48 of the closure 46. As the closure 46 telescopes on the container 12, the wedge-shaped edge 61 comes into contact with the barrier 20. A further pressure is applied the edge 61 ruptures the barrier 20 causing the barrier 20 and the test article 38 to fall into the sealed chamber 68 and into the medium 24. The exterior side 63 of the skirt 60 comes into frictional engagement with the interior of the side wall 16 of the container 12. The exterior of the side wall 16 comes into frictional engagement with the interior side of the first section 56 of the wall 50 of the closure 46. As the closure 46 telescopes on the container 12 and as the open end 18 comes into contact with the top portion 48 a seal is formed as shown in FIG. 10.

In FIGS. 11–16 a third embodiment of the invention is shown. The test vial 70 includes an initially open container 72, a barrier 80, and a closure 100. The container 72 generally has a closed end 74, side wall 76, and an open end 78. The open end 78 has a lip 79 which extends radially inward at an acute angle. The container 72 can also have a neck 75 which is positioned adjacent the open end 78. The circumference of the neck 75 is smaller than the circumference of the open end 78.

The barrier 80 is positioned between the neck 75 and the lip 79 of the open end 78. The barrier 80 can be made of any substantially impermeable, rupturable material. In a preferred embodiment the container 72 and the barrier 80 comprises an integrally molded polypropylene vial whose side wall 76, closed end 74 and barrier 80 define a sealed chamber 82. The barrier 80 is defined by an annular sealing member 84, a frangible support membrane 86 and a test article support 88. The barrier 80 acts to confine within the sealed chamber 82 a measured quantity of the fluid medium 24.

The annular sealing member 84 is positioned immediately adjacent the interior of the side wall 76. The sealing member 84 is positioned between the lip 79 and the neck 75 of the open end 78. The sealing member 84 can have exterior sides 90, 91, 92, 93 which matingly engage the interior of the side wall 76. The exterior sides 90, 91, 92, 93 act to form a tight seal with the wall 76 of the container 72.

The sealing member 84 has interior sides 95, 96 and 97. The interior side 95 is positioned at an acute angle to the exterior side 90. The interior side 95 is disposed at such an angle to facilitate the movement of the outside environment through the open chamber 99. The sealing member 84 can have a interior side 95 which is disposed at a greater angle (not shown) to increase the movement of the environment through the open chamber 99.

The membrane 86 is positioned between the interior sides 96 and 97. The membrane 86 extends radially towards the test article support 88. The membrane 86 is sufficiently thin such that it may be easily punctured or ruptured. The membrane 86 must also be thick enough to hold the test article support 88 in position. The test article support 88 is held in position in substantially the center of the open end 78 of the container 72 by the membrane 86. In a preferred embodiment the test article support 88 is shown as having a dish shape. The test article 38 is positioned on the test article support 88. The dish shape of the test article support 88 allows the test vial 70 to be used without a test article 38. The sample of the environment can be collected in the dish shaped surface of the support 88.

The closure 100 is positioned adjacent the open end 78 and the barrier means 80 of the container 72. The closure 100 is constructed to axially fit around the open end 78 of the container 72. The closure 100 can generally be made of any substantially hard material. In a preferred embodiment the closure 100 is made of a polycarbonate material.

The closure 100 includes a top portion 102, side walls 104, retaining means 106, and detaching member 108. The closure 100 is positioned adjacent the open end 78 such that the side wall 104 extends from the top portion 102 in a direction towards the closed end 74 of the container 72.

The top portion 102, the side wall 104 and the barrier 80 define the open chamber 99. The open chamber 99 is in communication with the outside environment. The closure 100 is held in a first position by the retaining ribs 106. The retaining ribs 106 includes a plurality of ridges 110 on the closure 100 and a detent 112 on the closure container 72. The ridges 110 are positioned on the interior side of the wall 104. The ridges 110 radially extend inward. The ridges 110 define a plurality of recesses 114, as best seen in FIG. 14, on the interior of the side wall 104. The recesses 114 allow the environment to flow into the open chamber 99.

The detent 112 is positioned on the exterior side of the container 72. The detent 112 is adjacent the open end 78 of the container 72. The ridges 110 and detent 112 act to hold the closure 100 in frictional engagement against the lip 79 of the container 72 when the closure 100 is in the first position.

Detaching member 108 extends axially from the top portion 102 of the closure 100 in a direction towards the barrier 80. The detaching member 108 includes a depending annular skirt 116, a leading edge 118 and a contact member 120. In a preferred embodiment, the detaching member 108 can be positioned substantially closer to the barrier 80 for ease of manufacturing.

Figure 17:
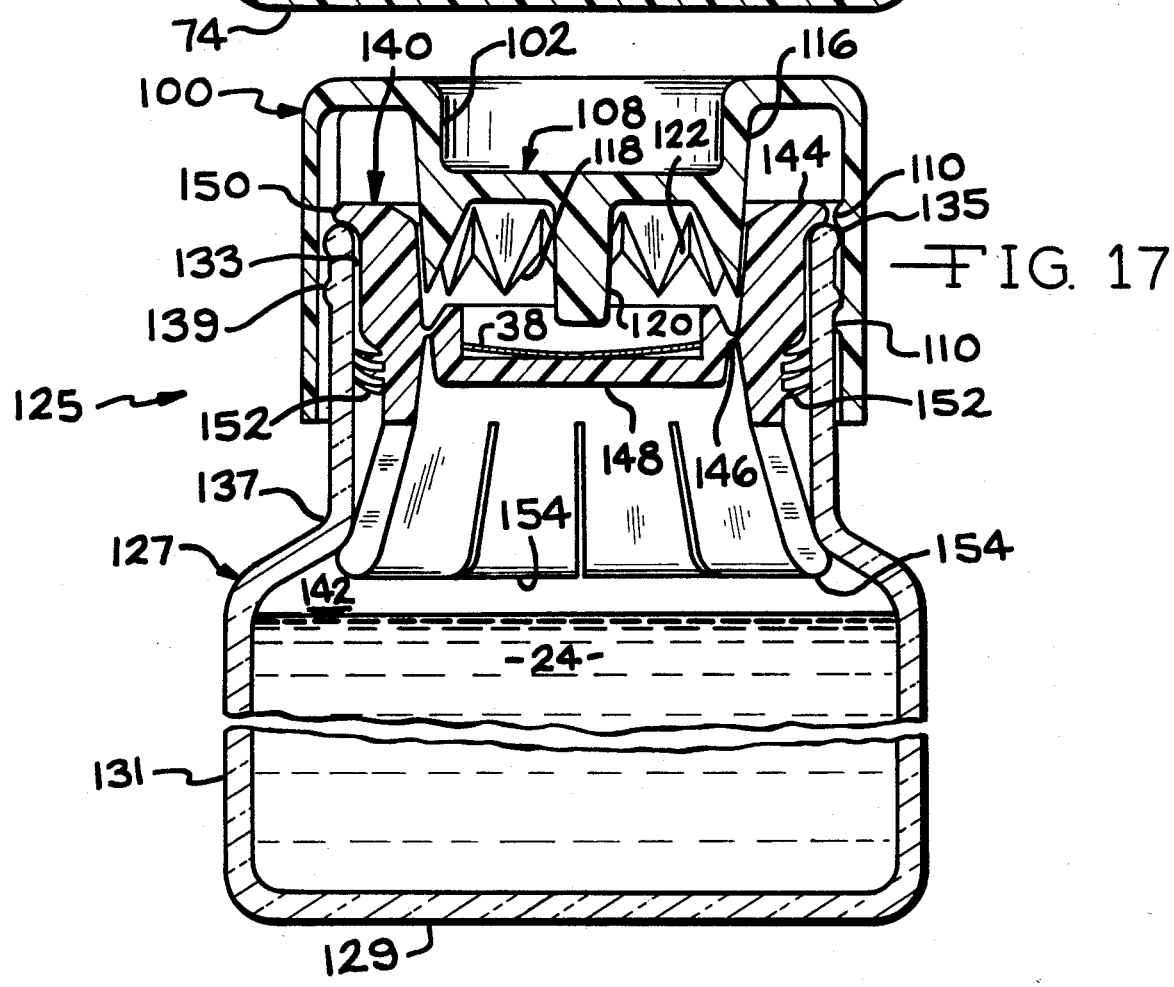
FIG. 17 is an elevation view, in cross-section, of a fourth embodiment of the invention.

The depending annular skirt 116 extends from the top portion 102 at a slight angle. The angle of the depending skirt 116 is complementary to the angle of the interior side 96 of the sealing member 84 of the barrier 80. The leading edge 118 is positioned at the end of the skirt 116 that is nearest the barrier 80. The leading edge 118 contains a plurality of cutting surfaces 122. In a preferred embodiment the cutting surfaces 122 are positioned to form individual wedges or teeth, as shown in FIGS. 15–17.

The contact member 120 extends axially from substantially the center of the top portion 102 of the closure 100 in a direction towards the barrier 80. The contact member 120 extends beyond the leading edge 18. The contact member 120 can have a substantially cylindrical shape.

In operation, manual pressure is applied to the top portion 102 of the closure 100. As the closure 100 telescopes on the container 72, the contact member 120 strikes the test article 38 and the middle of the test article support 88. As further pressure is applied, the contact member 120 pushes against the test article support 88 and stretches the membrane 86. The depending annular skirt 116 comes into sliding engagement with the interior side 96 of the sealing member 84. The leading edge 118 and the cutting surfaces 122 come into contact with the membrane 86. As further pressure is applied the leading edge 118 and the cutting surfaces 122 puncture the membrane 86. The skirt 116 moves along the interior side 96 and forms a seal with the test article support 88. As the closure 100 continues to telescope on the container 72 the leading edge 118 and the cutting surfaces 122 rupture the membrane 86 causing the test article support 88 and the article 38 to fall into the sealed chamber 82 and into the fluid medium 24.

In this embodiment the container 72 may be made of glass. In a preferred embodiment of the invention the test vial 70 may be formed by a blow mold process. In the blow mold process the container 72 is formed, filled with the fluid medium 24, and sealed with the barrier 80 in a continuous process. The container 72 can be stored for long periods of time. The container 72, the test article 38, and the closure 100 can be assembled at a later point in time. The container 72 and the barrier 80 can be made of a substantially translucent, moldable plastic material such as polypropylene. The closure 100 can be made of a plastic material that will retain a sharp edge, such as a polycarbonate material. In addition, the polycarbonate closure 100 can be color-coded to aid in the identification of the particular test article 38 and fluid medium 24 being used.

In FIG. 17 a fourth embodiment of the invention is shown. The test vial 125 includes the closure 100 of the third embodiment, an initially open container 127, and a barrier 140. The container 127 generally has a closed end 129, side walls 131, and an open end 133. The open end 133 has a lip 135 which extends radially outward. The container 127 has a neck 137. The neck 137 has a circumference which is smaller than the circumference of the sealed chamber 142. In this embodiment the container 127 can be made of glass.

The barrier 140 is positioned adjacent the open end 133 and the lip 135 of the container 127. The barrier 140, the side wall 131 and the closed end 129 of the container 127 define a sealed chamber 142. The barrier 140 acts to confine within the sealed chamber 142 a measured quantity of the fluid medium 24. The barrier 140 has an annular sealing member 144, a membrane 146 and a test article support 148.

The annular sealing member 144 is positioned adjacent the interior of the side wall 127. The sealing member 144 has a lip 150, at least one fin 152 and a plurality of flanges 154. The lip 150 radiates outwardly and is positioned adjacent the lip 135 of the container 127. The lip 150 acts to hold the barrier 140 in position on the open end 133 of the container 127. The fin 152 extends from the exterior side of the sealing member 144 in a direction towards the side wall 131 of the container 127. The fin 152 can extend radially towards the side wall 131 of the container 127. Alternatively, the fin 152 can extend in a downward direction (not shown) towards the side wall 131. The fin 152 acts to form a seal when the barrier 140 is positioned in the open end 133 of the container 127.

The plurality of flanges 154 extends from the sealing member 144 in a direction towards the neck 137 of the container 127. The lower portion of the flanges 154 defines a circumference greater than the circumference of the neck 137. The flanges 154 are flexible such that the barrier 140 can be easily inserted into the container 127. The flanges 154 act to hold the barrier 140 in position in the container 127.

When the closure 100 is in the second position, (not shown) the ridges 110 of the closure 100 engage a ridge 139 on the container 127. The ridge 139 extends radially from the exterior of the side wall 131. The ridge 139 extends substantially around the exterior of the side wall 131 such that the ridges 110 engage the ridge 139 at all times when the closure 100 is in the second position.

The above-identified description of the invention is given only for the sake of explanation. Various modifications and substitutions, other than those cited, can be made without departing from the scope of the invention as defined in the following claims.

What we claim is:

1. A test vial, comprising, in combination:
an article for immersion into a fluid medium;
a sealed chamber containing said fluid medium;
an open chamber, said open chamber being external to said sealed chamber;
said open and sealed chambers defining a barrier, said barrier isolating said fluid medium from said open chamber;
a closure, said closure covering said open chamber;
retaining means, said retaining means being on said open chamber and on said closure, said retaining means cooperatively supporting said closure in a first position, said retaining means including a plurality of longitudinal ribs positioned on the interior of said closure, said longitudinal ribs frictionally engaging the exterior of said sealed chamber;
said retaining means cooperatively receiving said closure in a second position; and
means on said closure for detaching said barrier from said open chamber and said sealed chamber, said detaching means having a frustroconical shape, said detaching means injecting said article into said fluid medium upon movement of said closure from said first position to said second position, said detaching means acting to seal said sealed chamber after said barrier is detached.

2. A test vial, comprising, in combination;
an article for immersion into a fluid medium;
a sealed chamber containing said fluid medium;
an open chamber, said open chamber being external to said sealed chamber, said open chamber containing said article;
said sealed and opened chambers defining a barrier, said barrier isolating said fluid medium from said article;
a closure, said closure covering said open chamber;
retaining means, said retaining means being on said open chamber and on said closure, said retaining means cooperatively supporting said closure means in a first position, said retaining means including a plurality of longitudinally extending ribs, said longitudinally extending ribs being positioned on a portion of an interior wall of said closure;
said retaining means cooperatively receiving said closure in a second position; and
means on said closure for detaching said barrier from said open chamber and said sealed chamber, said detaching means extending from said closure in a direction towards said barrier, said detaching means including a depending skirt member, a lower portion of said depending skirt member including an edge, said edge having a wedge-shape, said wedge-shaped edge acting to detach said barrier upon movement of said closure from said first position to said second position, said detaching means injecting said article into said fluid medium upon movement of said closure from said first position to said second position.

3. A test vial, comprising, in combination:
an article for immersion into a fluid medium;
a sealed chamber containing said fluid medium;

an open chamber, said open chamber being external to said sealed chamber, said open chamber containing said article;

said sealed and open chambers defining a barrier, said barrier isolating said fluid medium from said article, said barrier including a sealing member, a membrane member and support member, said sealing member being positioned substantially adjacent the interior side of said open chamber, said sealing member frictionally engaging said interior side of said open chamber, said membrane member being positioned on said sealing member opposite the side engaging the open chamber, said membrane member extending radially inward, said membrane member being substantially thin, said membrane member being capable of being readily broken, said membrane member being connected to said support member, said membrane member substantially surrounding the support member, said membrane member connecting said sealing member to said support member;

said sealing member including a plurality of surfaces on said exterior side of said sealing member, said plurality of exterior surfaces matingly engaging a plurality of surfaces on the interior of said open chamber, said surfaces acting to form a seal;

said sealing member further including a plurality of interior surfaces, said interior surfaces being disposed at an angle to frictionally engage a detaching means when said closure is moved to said second position;

retaining means, said retaining means being on said open chamber and on said closure, said retaining means cooperatively supporting said closure in a first position, said retaining means including a plurality of rib members, said rib members extending radially along the interior of said closure, said rib members engaging at least one ridge member on the exterior of said open chamber, said ridge member and said rib members cooperatively supporting said closure means in said first position, said ridge member and said rib members cooperatively holding said closure in said second position, said rib members defining a plurality of recesses, said recesses allowing said open chamber to be in communication with said outside environment when closure is in said first position; and means on said closure for detaching said barrier from said open chamber and said sealed chamber, said detaching means injecting said article into said fluid medium upon movement of said closure from said first position to said second position said detaching means having a depending skirt member, said depending skirt member having a leading edge, said leading edge having a plurality of wedge-shape surfaces, said wedge-shaped surfaces acting to puncture said barrier, said detaching means further including a contact member, said contact member extending axially from said detaching means in a direction towards said barrier, said contact member injecting said barrier into said sealed chamber when said closure is moved to said second position.

4. The test vial of claim 3 wherein said barrier further includes at least one fin member, and a plurality of flange members, said fin member extending from said sealing member in a direction towards said open chamber, said fin member frictionally engaging said open chamber, said fin member acting to seal said fluid medium within said sealed chamber;

said plurality of flange members extending from said sealing member in a direction towards said open chamber, said flange members being disposed at an angle such that said flange members engage the interior of said sealed chamber, said flange members acting to position said closure adjacent said open chamber.

* * * * *